(12) United States Patent
McGrath et al.

(10) Patent No.: US 12,406,773 B2
(45) Date of Patent: Sep. 2, 2025

(54) TRANSFERRING INFORMATION THROUGH KNOWLEDGE GRAPH EMBEDDINGS

(71) Applicant: Accenture Global Solutions Limited, Dublin (IE)

(72) Inventors: Rory McGrath, Kildare Town (IE); Xu Zheng, Dublin (IE); Jeremiah Hayes, Dublin (IE)

(*) Notice: Subject to any disclaimer, the term of this patent is extended or adjusted under 35 U.S.C. 154(b) by 612 days.

(21) Appl. No.: 17/821,910

(22) Filed: Aug. 24, 2022

(65) Prior Publication Data

US 2024/0071629 A1 Feb. 29, 2024

(51) Int. Cl.
*G16H 70/40* (2018.01)
*G06N 5/022* (2023.01)
*G16C 20/70* (2019.01)

(52) U.S. Cl.
CPC .............. *G16H 70/40* (2018.01); *G06N 5/022* (2013.01); *G16C 20/70* (2019.02)

(58) Field of Classification Search
CPC ......... G16H 70/40; G16C 20/70; G06N 5/022
USPC ........................................................ 706/46
See application file for complete search history.

(56) References Cited

U.S. PATENT DOCUMENTS

| | | | |
|---|---|---|---|
| 11,080,607 B1* | 8/2021 | Demtchenko | G06N 3/044 |
| 11,264,140 B1* | 3/2022 | Tal | G16H 50/20 |
| 12,288,389 B2* | 4/2025 | Min | G06N 3/088 |
| 2021/0081717 A1* | 3/2021 | Creed | G06N 5/022 |
| 2022/0188654 A1* | 6/2022 | Knuff | G06N 3/047 |
| 2022/0261668 A1* | 8/2022 | Stumpe | G06F 16/284 |
| 2022/0351053 A1* | 11/2022 | Norvaisas | G06N 7/01 |

FOREIGN PATENT DOCUMENTS

WO    WO-2019220128 A1 * 11/2019 ............ G06N 3/082

OTHER PUBLICATIONS

IMohamed et al., "Discovering protein drug targets using knowledge graph embeddings", Bioinformatics, 36(2), 2020, 603-610, Aug. 1, 2019 (Year: 2019).*

MacLean et al., Knowledge graphs and their application in drug Expert opinion on drug discovery, 2021, vol. 16, No. 9, 1057-1069 (Year: 2021).*

(Continued)

*Primary Examiner* — Tsu-Chang Lee

(57) ABSTRACT

A device may receive a knowledge graph and SMILE data identifying compounds, and may train embeddings based on the knowledge graph. The device may generate graph embeddings for the SMILE data based on the embeddings, and may encode the SMILE data into a latent space. The device may combine the graph embeddings and the latent space to generate a combined latent-embedding space, and may decode the combined latent-embedding space to generate decoded SMILE data. The device may utilize the decoded SMILE data to train an encoder, and may process source SMILE data, with the trained encoder, to generate a source combined latent-embedding space. The device may search the source combined latent-embedding space to identify new SMILE data, and may decode the new SMILE data to generate decoded new SMILE data. The device may evaluate the decoded new SMILE data to identify particular SMILE data associated with a new compound.

20 Claims, 12 Drawing Sheets

(56) References Cited

OTHER PUBLICATIONS

Zeng et al., "Toward better drug discovery with knowledge graph", Current opinion in structural biology, 2022, 72:114-126 (Year: 2022).*

Karim et al., "Drug-drug interaction prediction based on knowledge graph embeddings and convolutional-LSTM network", ACM-BCB '19, Sep. 7-10, 2019, Niagara Falls, NY, USA (Year: 2019).*

* cited by examiner

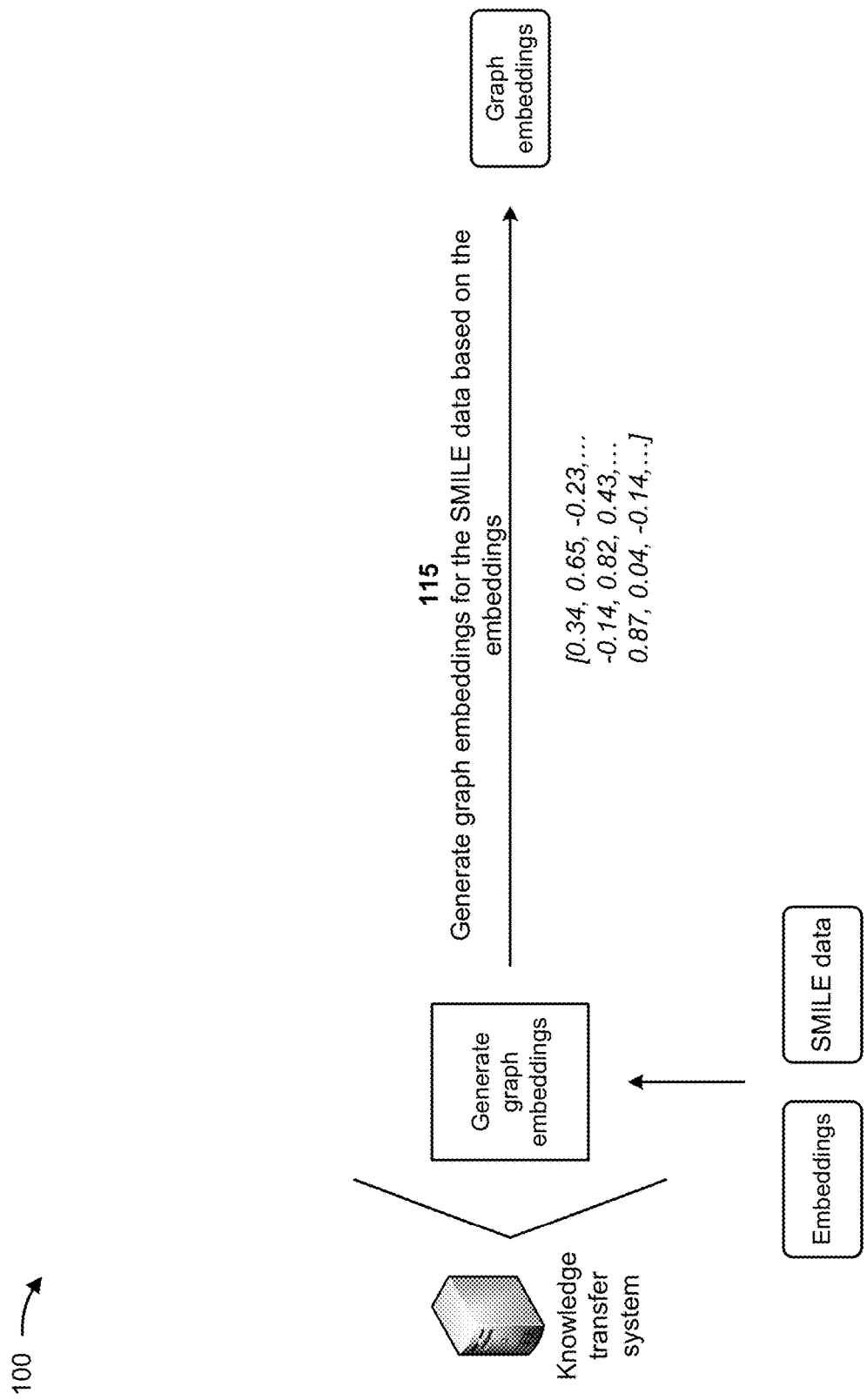

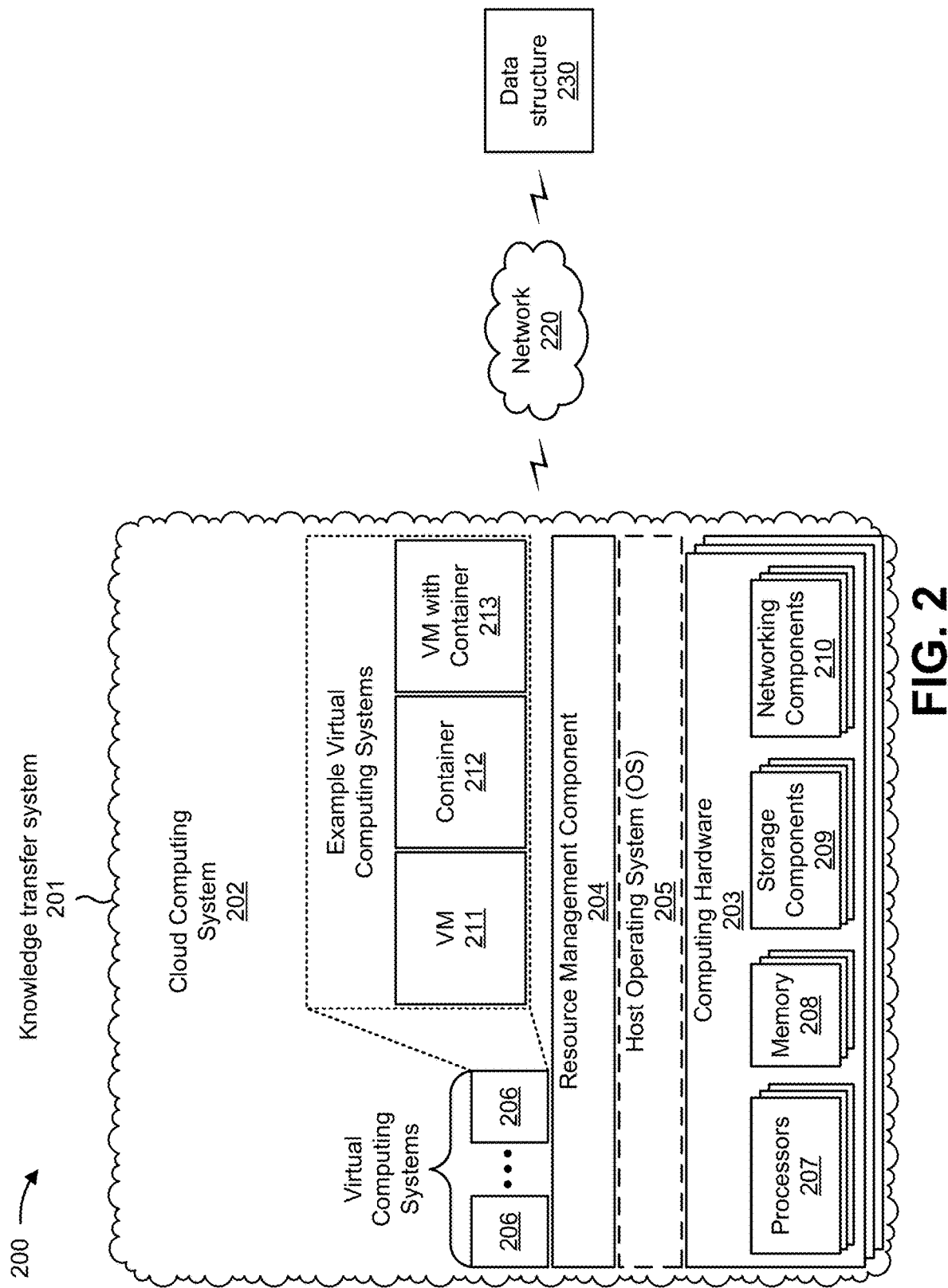

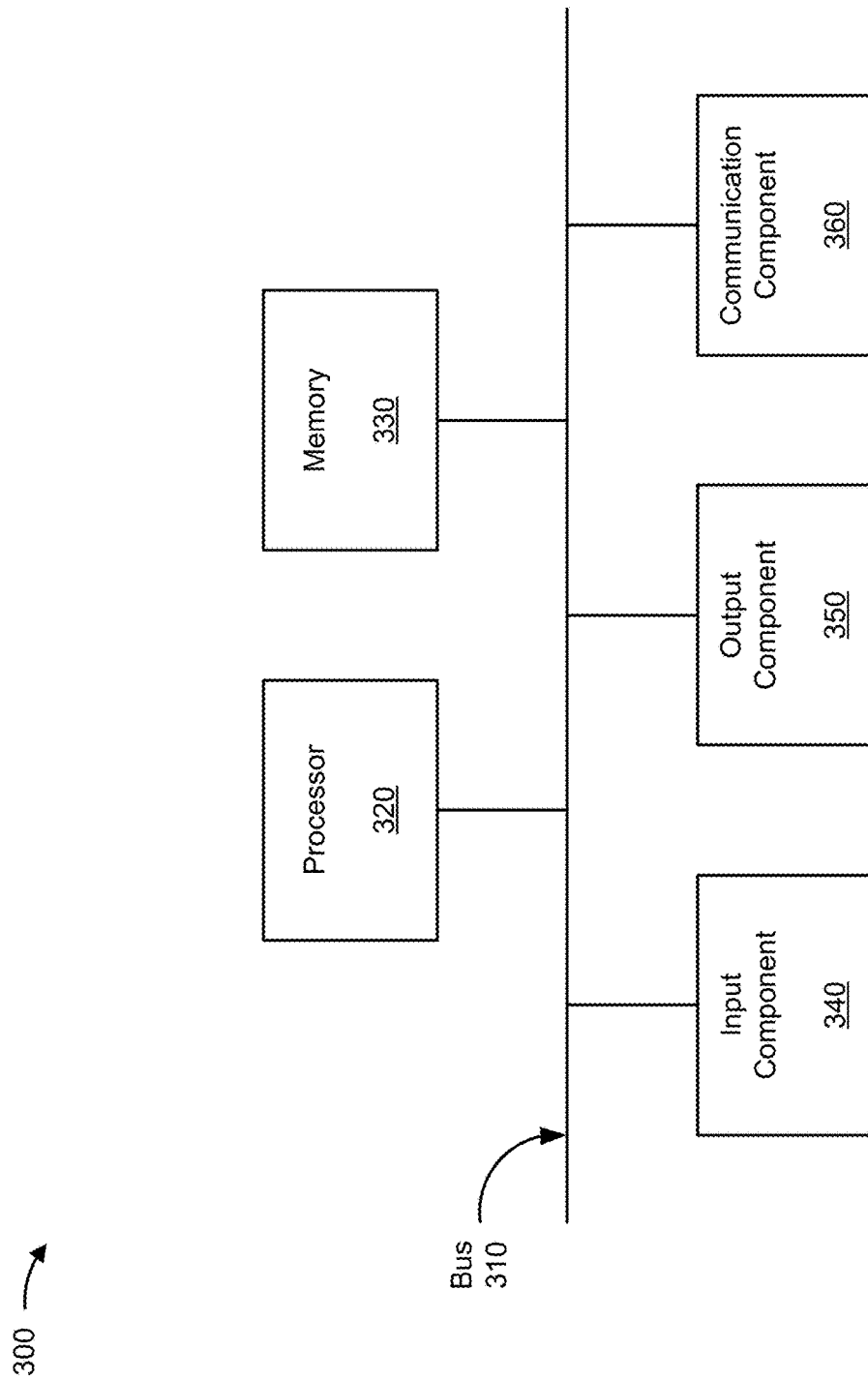

TRANSFERRING INFORMATION THROUGH KNOWLEDGE GRAPH EMBEDDINGS

BACKGROUND

Current methods of new drug discovery are time consuming and expensive. Machine learning may be utilized to discover new drugs. Machine learning is a type of artificial intelligence that allows software applications to become more accurate at predicting outcomes without being explicitly programmed.

SUMMARY

Some implementations described herein relate to a method. The method may include receiving a knowledge graph representing information and simplified molecular-input line-entry (SMILE) data identifying compounds, and training embeddings based on the knowledge graph. The method may include generating graph embeddings for the SMILE data based on the embeddings, and encoding the SMILE data into a latent space. The method may include combining the graph embeddings and the latent space to generate a combined latent-embedding space, and decoding the combined latent-embedding space to generate decoded SMILE data. The method may include utilizing the decoded SMILE data to train an encoder and to generate a trained encoder, and processing source SMILE data, with the trained encoder, to generate a source combined latent-embedding space. The method may include searching the source combined latent-embedding space to identify new SMILE data associated with new compounds, and decoding the new SMILE data to generate decoded new SMILE data. The method may include evaluating the decoded new SMILE data to identify particular SMILE data associated with a new compound.

Some implementations described herein relate to a device. The device may include one or more memories and one or more processors coupled to the one or more memories. The one or more processors may be configured to receive a knowledge graph representing information and SMILE data identifying compounds, and train embeddings based on the knowledge graph. The one or more processors may be configured to generate graph embeddings for the SMILE data based on the embeddings, and combine the graph embeddings and the latent space to generate a combined latent-embedding space. The one or more processors may be configured to decode the combined latent-embedding space to generate decoded SMILE data, and utilize the decoded SMILE data to train an encoder and to generate a trained encoder. The one or more processors may be configured to process source SMILE data, with the trained encoder, to generate a source combined latent-embedding space, and search the source combined latent-embedding space to identify new SMILE data associated with new compounds. The one or more processors may be configured to decode the new SMILE data to generate decoded new SMILE data, and evaluate the decoded new SMILE data to identify particular SMILE data associated with a new compound. The one or more processors may be configured to convert the particular SMILE data into triples, and update the knowledge graph based on the triples.

Some implementations described herein relate to a non-transitory computer-readable medium that stores a set of instructions for a device. The set of instructions, when executed by one or more processors of the device, may cause the device to receive a knowledge graph representing information and SMILE data identifying compounds, and train embeddings based on the knowledge graph. The set of instructions, when executed by one or more processors of the device, may cause the device to generate graph embeddings for the SMILE data based on the embeddings, and encode the SMILE data into a latent space. The set of instructions, when executed by one or more processors of the device, may cause the device to combine the graph embeddings and the latent space to generate a combined latent-embedding space, and decode the combined latent-embedding space to generate decoded SMILE data. The set of instructions, when executed by one or more processors of the device, may cause the device to utilize the decoded SMILE data to train an encoder and to generate a trained encoder, and process source SMILE data, with the trained encoder, to generate a source combined latent-embedding space. The set of instructions, when executed by one or more processors of the device, may cause the device to search the source combined latent-embedding space to identify new SMILE data associated with new compounds, and decode the new SMILE data to generate decoded new SMILE data. The set of instructions, when executed by one or more processors of the device, may cause the device to evaluate the decoded new SMILE data to identify particular SMILE data associated with a new compound, and convert the particular SMILE data into triples. The set of instructions, when executed by one or more processors of the device, may cause the device to update the knowledge graph based on the triples, and evaluate the decoded new SMILE data to identify additional SMILE data. The set of instructions, when executed by one or more processors of the device, may cause the device to store the additional SMILE data.

BRIEF DESCRIPTION OF THE DRAWINGS

FIGS. 1A-1I are diagrams of an example implementation described herein.

FIG. 2 is a diagram of an example environment in which systems and/or methods described herein may be implemented.

FIG. 3 is a diagram of example components of one or more devices of FIG. 2.

DETAILED DESCRIPTION

Figure 1A:
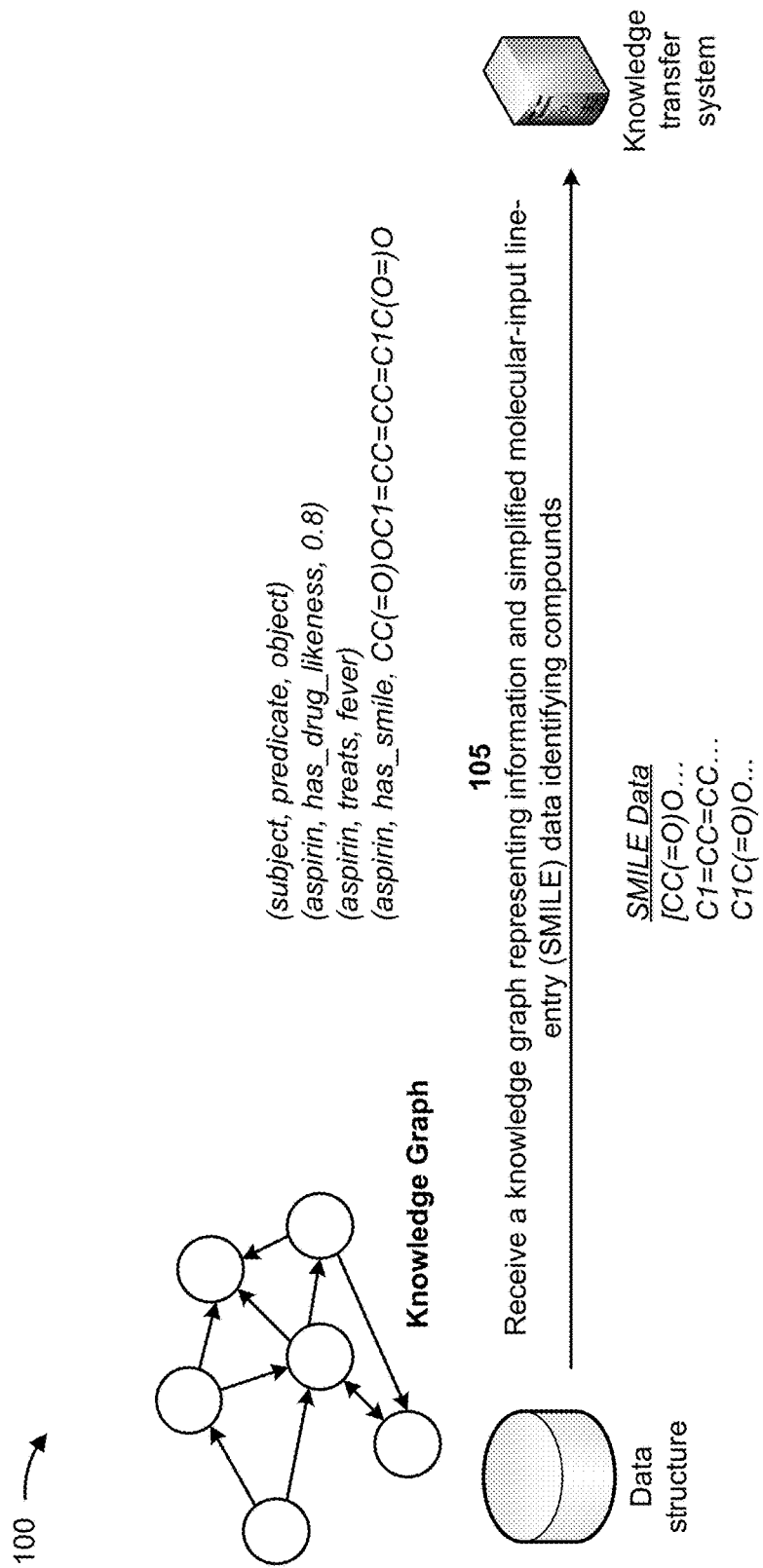

The following detailed description of example implementations refers to the accompanying drawings. The same reference numbers in different drawings may identify the same or similar elements.

Machine learning may be utilized for early identification of drugs (e.g., compounds) with a greatest probability of being safe and effective, and for discerning and discarding potential compounds that are likely to fail at later stages of drug development. Current work in the field of drug discovery creates a latent space by training a variational autoencoder (VAE) or by training a VAE while jointly selecting a property to guide creation of the latent space and to enable property prediction. However, as more properties are simultaneously utilized, more data is required to train the VAE. This is because each property requires an output layer with trainable parameters and requires inclusion in an overall loss function when training the VAE. For example, if a latent space includes five properties, the VAE may require six separate output layers. The first five output layers may map to the five properties and the sixth output layer may be utilized for decoding SMILE data. Such an arrangement may increase a quantity of trainable parameters and may add complications to the loss function. Utilization of more properties may improve the latent space for drug discovery, but may make training of the VAE infeasible.

Therefore, current techniques for utilizing machine learning to discover new drugs consume computing resources (e.g., processing resources, memory resources, communication resources, and/or the like), networking resources, and/or the like associated with improperly training a machine learning model, failing to identify new drugs based on the improperly trained machine learning model, incorrectly identifying new drugs based on the improperly trained machine learning model, performing useless research and development on incorrectly identified new drugs, and/or the like.

Some implementations described herein relate to a knowledge transfer system that transfers information through knowledge graph embeddings. For example, the knowledge transfer system may receive a knowledge graph representing information and SMILE data identifying compounds, and may train embeddings based on the knowledge graph. The knowledge transfer system may generate graph embeddings for the SMILE data based on the embeddings, and may encode the SMILE data into a latent space. The knowledge transfer system may combine the graph embeddings and the latent space to generate a combined latent-embedding space, and may decode the combined latent-embedding space to generate decoded SMILE data. The knowledge transfer system may utilize the decoded SMILE data to train an encoder and to generate a trained encoder, and may process source SMILE data, with the trained encoder, to generate a source combined latent-embedding space. The knowledge transfer system may search the source combined latent-embedding space to identify new SMILE data associated with new compounds, and may decode the new SMILE data to generate decoded new SMILE data. The knowledge transfer system may evaluate the decoded new SMILE data to identify particular SMILE data associated with a new compound, and may convert the particular SMILE data into triples. The knowledge transfer system may update the knowledge graph based on the triples.

In this way, the knowledge transfer system transfers information through knowledge graph embeddings. The knowledge transfer system may represent all properties of SMILE data in a knowledge graph, and may reduce and represent all the properties in knowledge graph embeddings. Each of the knowledge graph embeddings may include the SMILE data in a vector of specified size. The knowledge transfer system may train a latent space to represent a structure of a property (e.g., a graph embedding) that includes all the properties of the SMILE data. The knowledge transfer system may generate the latent space based on all the properties of the SMILE data in a scalable and efficient manner. This, in turn, conserves computing resources, networking resources, and/or the like that would otherwise have been consumed in improperly training a machine learning model, failing to identify new drugs based on the improperly trained machine learning model, incorrectly identifying new drugs based on the improperly trained machine learning model, performing useless research and development on incorrectly identified new drugs, and/or the like.

FIGS. 1A-1I are diagrams of an example 100 associated with transferring information through knowledge graph embeddings. As shown in FIGS. 1A-1I, example 100 includes a knowledge transfer system associated with a data structure. The knowledge transfer system may include a system that transfers information through knowledge graph embeddings. Further details of the knowledge transfer system and the data structure are provided elsewhere herein.

As shown in FIG. 1A, and by reference number 105, the knowledge transfer system may receive a knowledge graph representing information and SMILE data identifying compounds. For example, a data structure (e.g., a database, a table, a list, and/or the like) may store the knowledge graph and/or the SMILE data. In some implementations, the knowledge transfer system may continuously receive the knowledge graph and/or the SMILE data from the data structure, may periodically receive the knowledge graph and/or the SMILE data from the data structure, may receive the knowledge graph and/or the SMILE data from the data structure based on providing a request to the data structure, and/or the like. The knowledge graph may include a graph dataset of directed, label edges that connect nodes representing concepts (e.g., people, products, companies, genes, proteins, and/or the like), a graph dataset of undirected, label edges that connect nodes, and/or the like. The knowledge graph may be utilized to represent biomedical datasets. The SMILE data may include specifications in the form of line notations for describing structures of chemical species (e.g., compounds) using short ASCII strings (e.g., CC(=O) OC1=CC=CC=C1C(=O)O). Although implementations are described in connection with SMILE data, the implementations may be utilized with any string-based representation of a compound, such as SMARTS, international chemical identifier (InChI), and/or the like.

In some implementations, the knowledge graph may represent a database of information about compounds (e.g., to be utilized for drug discovery). The knowledge graph may enable more properties and relationships around compounds to be represented, even properties and/or relationships that may not seem directly related to the compounds. Thus, the knowledge graph may address any confounding variables. Furthermore, the knowledge transfer system may utilize graph embeddings (e.g., which include all properties of compounds) when training a latent space instead of having to select a subset of properties due to data limitations.

The SMILE data may include SMILE representations of compounds and diseases treated by the compounds or biological pathways of the compounds. The SMILE data may be stored in an unstructured database, such as, for example, Stardog, Amazon Neptune, Neo4j, and/or the like. The knowledge graph may be represented as a set of triples. A triple is a fact or a link of the knowledge graph that is defined as t=(s, p, o), where s is a subject, p is a predicate, and o is an object. In one example, the triples may include the following information:

| Subject | Predicate | Object |
| --- | --- | --- |
| Aspirin | has drug likeness | 0.8 |
| Aspirin | has ease of synthesis | 0.9 |
| Aspirin | treats | fever |
| Aspirin | treats | arthritis |
| Aspirin | treats | migraine headaches |
| Aspirin | can cause | dry mouth |
| Aspirin | can cause | deafness |
| Aspirin | interacts with | anti-depressants |
| Aspirin | has SMILE | CC(=O)OC1=CC=CC=C1C(=O)O |
| Aspirin | was discovered | 1899 |

Figure 1B:
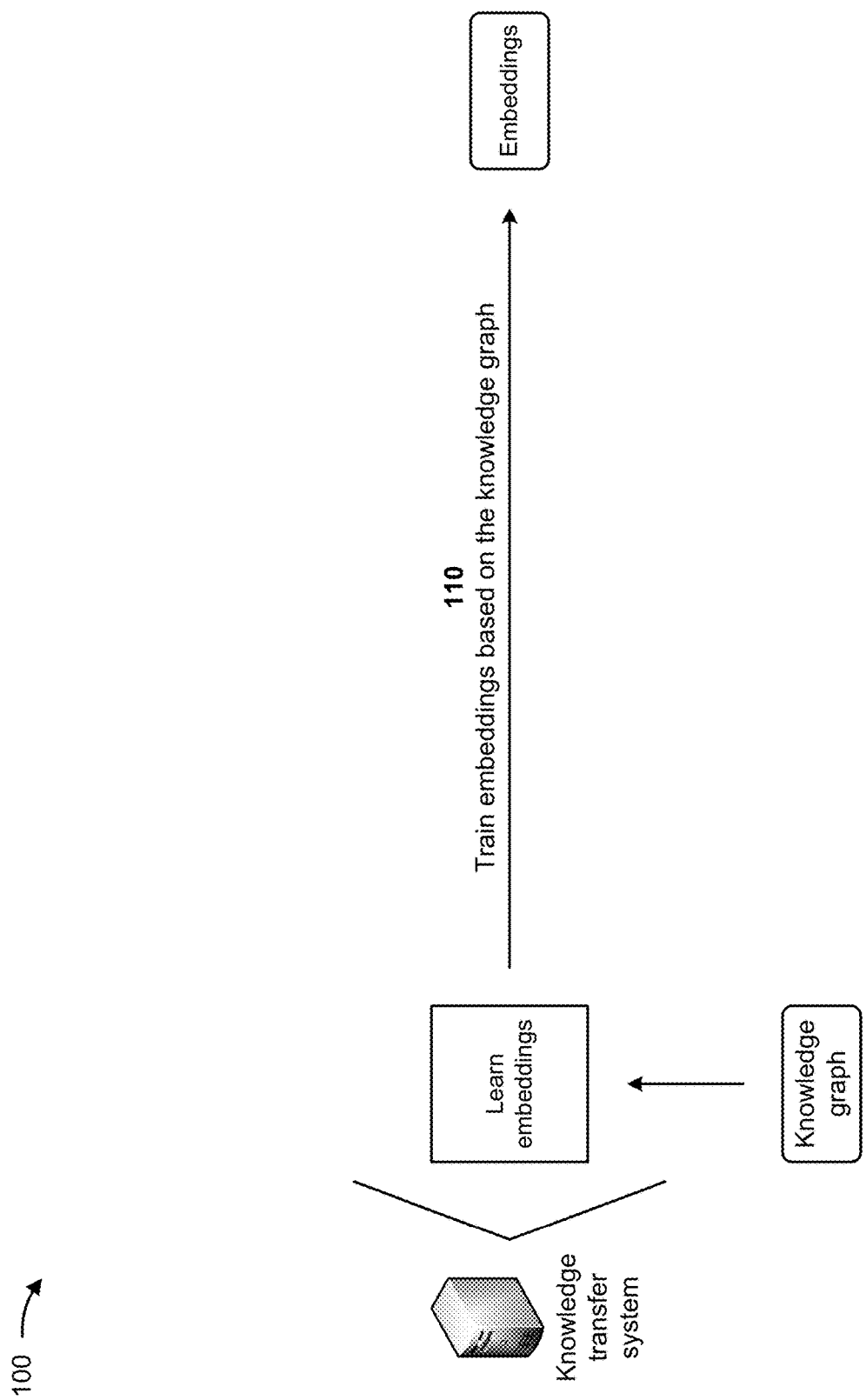

As shown in FIG. 1B, and by reference number 110, the knowledge transfer system may train embeddings based on the knowledge graph. For example, an embedding is a k-dimensional vector of real numbers that represents either a node or an edge type of the knowledge graph. In some implementations, the knowledge transfer system may utilize the knowledge graph and one or more techniques to train the embeddings. The techniques may include a DistMult technique (e.g., a neural tensor network with a diagonal matrix operator), a HolE technique (e.g., holographic embeddings technique), a ConvE technique (e.g., a convolutional two-dimensional knowledge graph embeddings technique), a ComplEx technique (e.g., a complex embeddings technique), and/or the like.

As shown in FIG. 1C, and by reference number 115, the knowledge transfer system may generate graph embeddings for the SMILE data based on the embeddings. For example, the knowledge transfer system may utilize the embeddings to generate graph embeddings for each compound specification of the SMILE data. In some implementations, the knowledge transfer system may convert each compound specification of SMILE data into a tensor of real values (e.g., a graph embedding). For example, as shown in FIG. 1C, a graph embedding may include tensor of real values, such as [0.34, 0.65, −0.23, . . . , −0.14, 0.82, 0.43, . . . , 0.87, 0.04, −0.14, . . . ]. Since generation of the graph embeddings is a deterministic process (e.g., and a training process to learn the graph embeddings is not a deterministic process), utilization of the graph embeddings may cause similar known compounds to be clustered together in a latent space based on properties of the compounds in the knowledge graph. A latent space is an abstract multi-dimensional space containing feature values that cannot be interpreted directly, but that encode a meaningful internal representation of externally observed events. Thus, instead of having to select which properties should be considered when determining a similarity between two compounds, the knowledge transfer system may utilize all properties of the compounds.

Figure 1D:
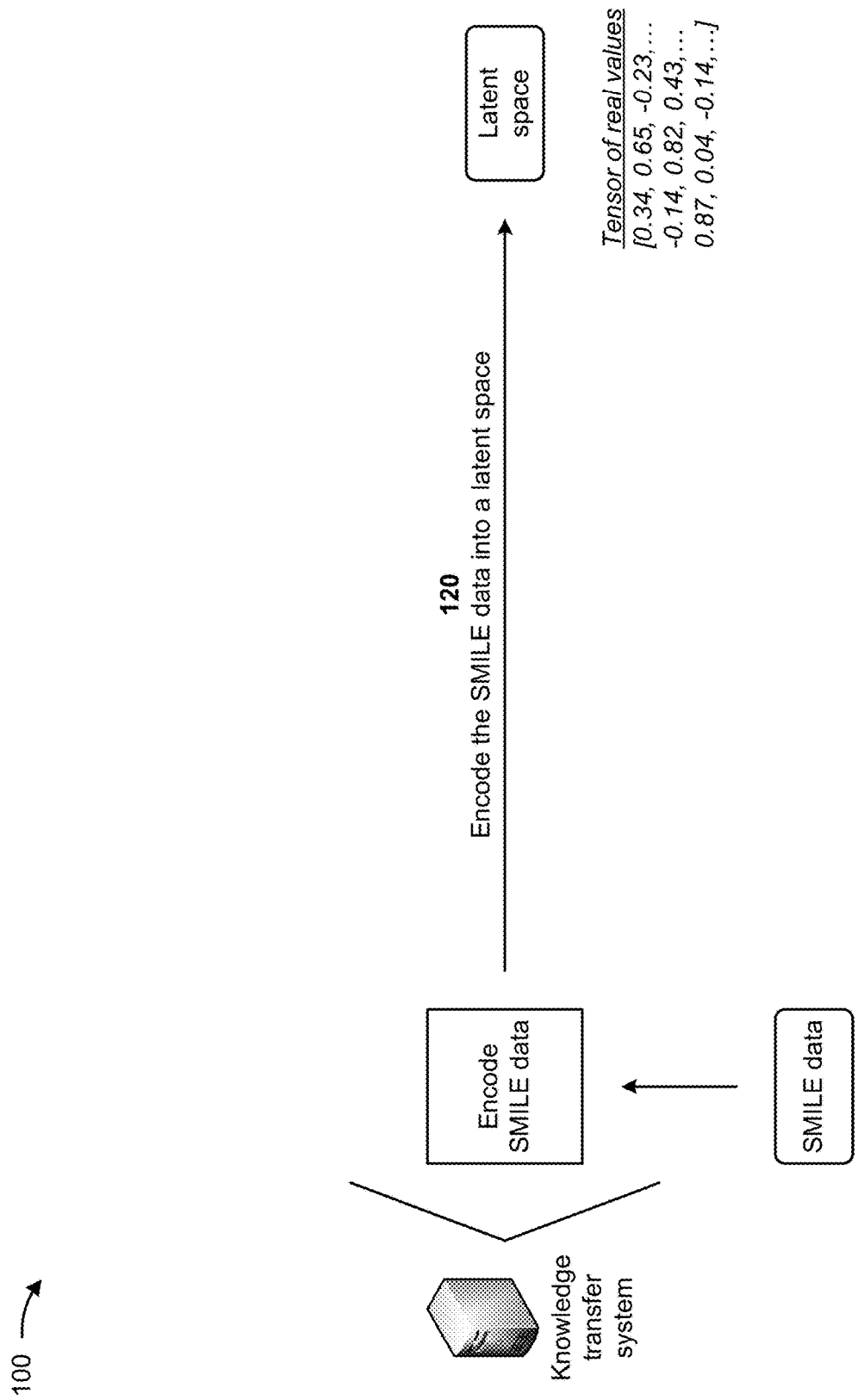

As shown in FIG. 1D, and by reference number 120, the knowledge transfer system may encode the SMILE data into a latent space. For example, the knowledge transfer system may train a neural network, a variational autoencoder (VAE), an adversarial autoencoder (AAE), a denoising autoencoder, a sparse autoencoder, a deep autoencoder, a contractive autoencoder, an undercomplete autoencoder, a convolutional autoencoder, variants of the aforementioned autoencoders, a generative adversarial network (GAN), and/or the like to encode the SMILE data into the latent space. Encoding the SMILE data into the latent space may encode the SMILE data into tensors of real values. In some implementations, a dimension of the latent space may be the same as a dimension of the graph embeddings. The latent space may include a continuous high dimensional space into which the SMILE data is projected. The latent space may accurately reconstruct the SMILE data and may group compound specifications of the SMILE data together based on structures of the SMILE data.

Figure 1E:
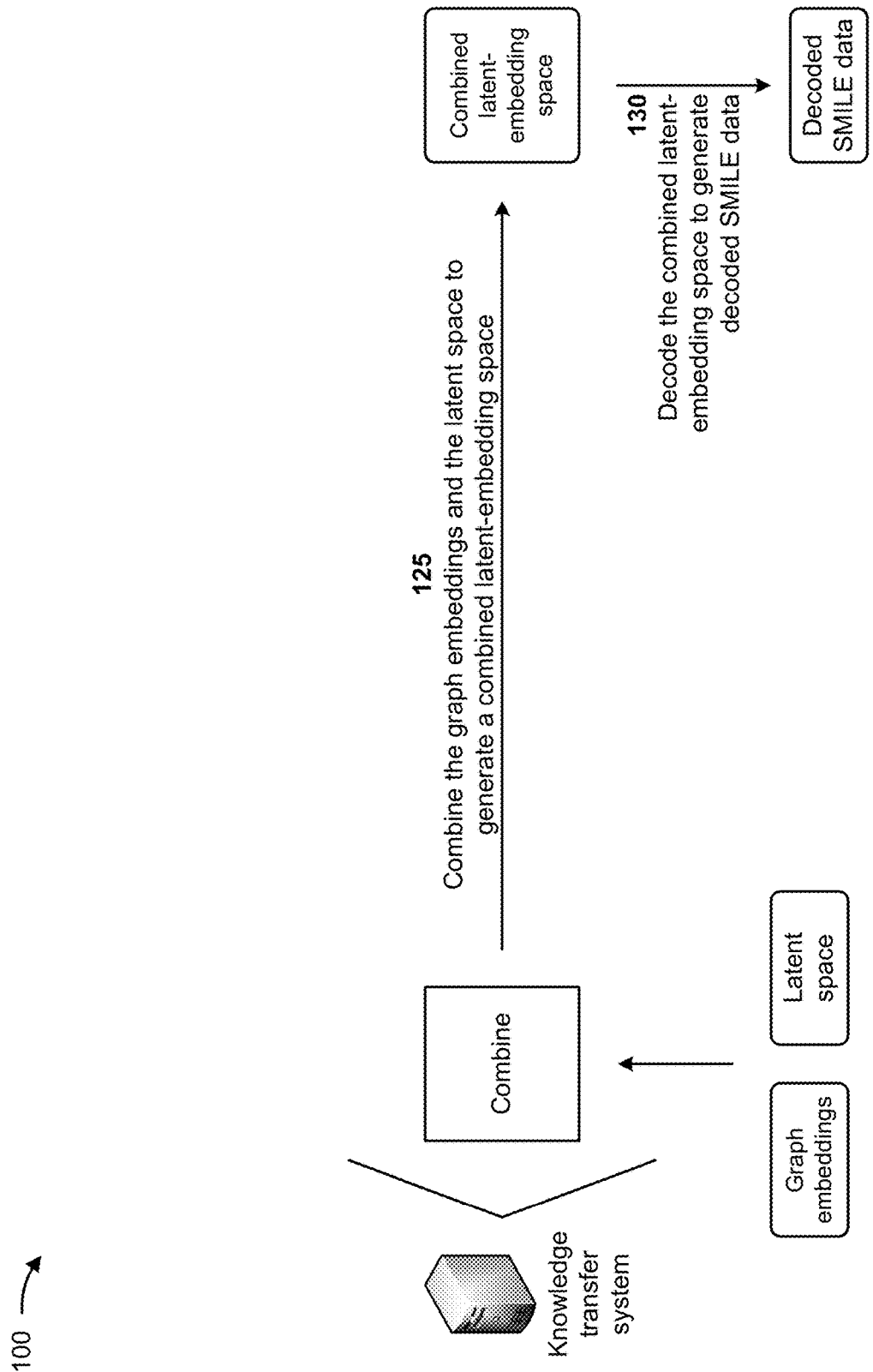

As shown in FIG. 1E, and by reference number 125, the knowledge transfer system may combine the graph embeddings and the latent space to generate a combined latent-embedding space. For example, the graph embeddings may cluster similar compounds together based on properties of the compounds and the latent space may cluster similar compounds together based on the SMILE data associated with the compounds. In some implementations, the knowledge transfer system may utilize a transformer to combine the graph embeddings and the latent space together to generate the combined latent-embedding space. A transformer is a deep learning model that utilizes a self-attention mechanism that differentially weights a significance of each portion of input data. A transformer may process an entire input all at once, and the self-attention mechanism may provide context for any position in an input sequence. In some implementations, when combining the graph embeddings and the latent space to generate the combined latent-embedding space, the knowledge transfer system may process the graph embeddings and the latent space, with a deep learning model, to generate the combined latent-embedding space. In some implementations, the combined latent-embedding space may include the properties of the graph embeddings and the properties of the latent space.

As further shown in FIG. 1E, and by reference number 130, the knowledge transfer system may decode the combined latent-embedding space to generate decoded SMILE data. For example, the knowledge transfer system may train a decoder to convert the tensors provided in the combined latent-embedding space back into compound specifications. The compound specifications may include the SMILE data (e.g., the decoded SMILE data) of original compounds.

Figure 1F:
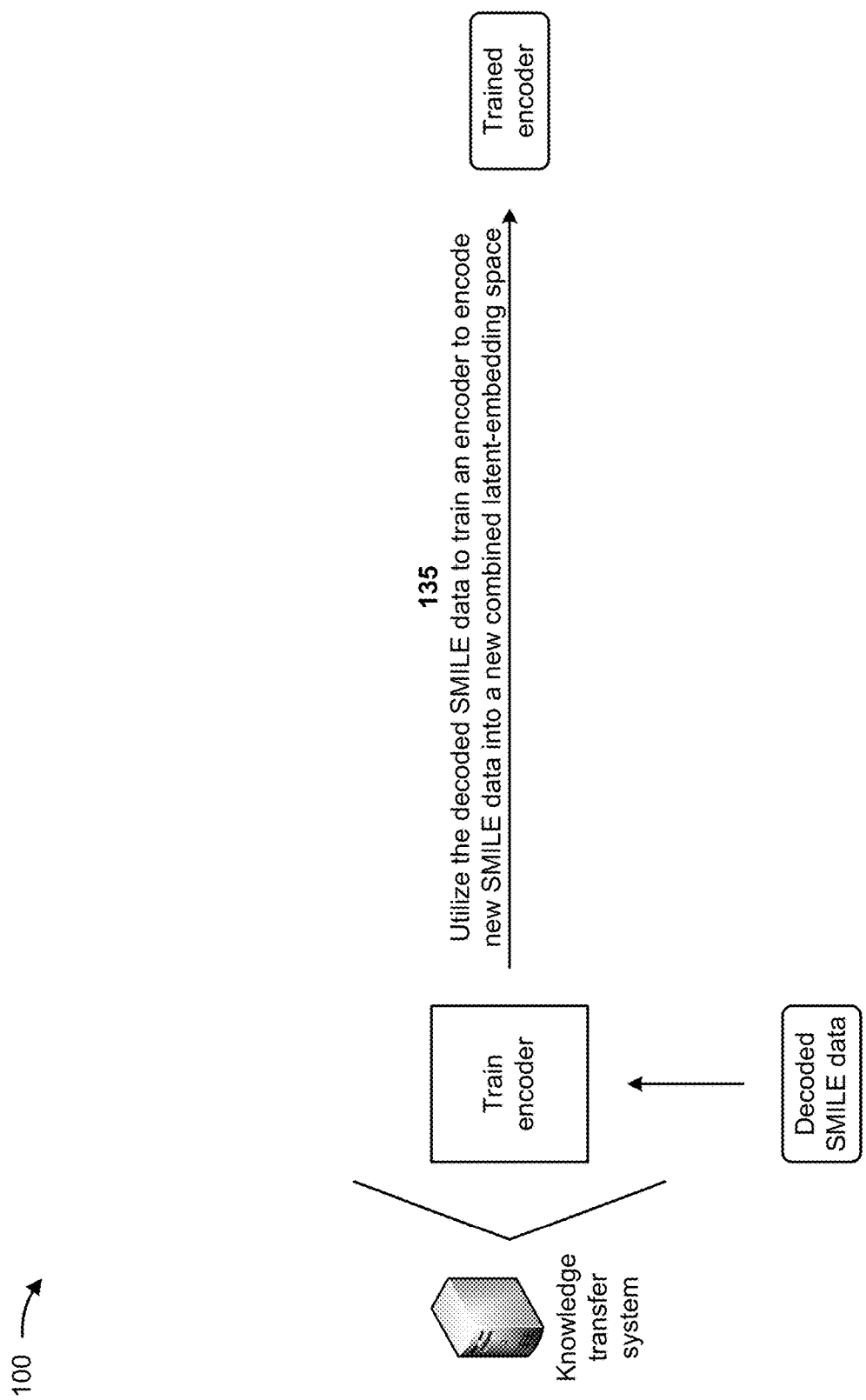

As shown in FIG. 1F, and by reference number 135, the knowledge transfer system may utilize the decoded SMILE data to train an encoder to encode new SMILE data into a new combined latent-embedding space. For example, the knowledge transfer system may train the encoder to encode new SMILE data directly into a new combined latent-embedding space. The knowledge transfer system may utilize the decoded SMILE data as training data for training the encoder. In some implementations, the knowledge transfer system need not train the decoder utilized to generate the decoded SMILE data.

In some implementations, the knowledge transfer system may train, validate, and/or test the encoder with the decoded SMILE data. For example, the knowledge transfer system may divide the decoded SMILE data into a first portion of decoded SMILE data, a second portion of decoded SMILE data, and a third portion of decoded SMILE data. The first portion, the second portion, and the third portion may include a same quantity of the decoded SMILE data, different quantities of the decoded SMILE data, and/or the like. In some implementations, more of the decoded SMILE data may be allotted to the first portion of decoded SMILE data since the first portion may be utilized to generate the training data set for the encoder.

The knowledge transfer system may generate a training dataset for the encoder based on the first portion of decoded SMILE data. The knowledge transfer system may generate a validation dataset for the encoder based on the second portion of decoded SMILE data. The knowledge transfer system may generate a test dataset for the encoder based on the third portion of decoded SMILE data. In other implementations, the knowledge transfer system may utilize different portions of the decoded SMILE data to generate the training dataset, the validation dataset, and/or the test dataset for the encoder.

In some implementations, the knowledge transfer system may train the encoder with the training dataset to generate a trained encoder, and may process the validation dataset, with the trained encoder, to validate that the trained encoder is operating correctly. If the trained encoder is operating correctly, the knowledge transfer system may process the trained encoder, with the test dataset, to further ensure that the trained encoder is operating correctly. A trained encoder can be said to be operating correctly if it has adequate accuracy, has adequate precision, has adequate recall, is not subject to excessive overfitting, and/or the like. If the trained encoder is operating excessively incorrect, the knowledge transfer system may modify the trained encoder and may revalidate and/or retest the modified encoder based on the validation dataset and/or the test dataset.

Figure 1G:
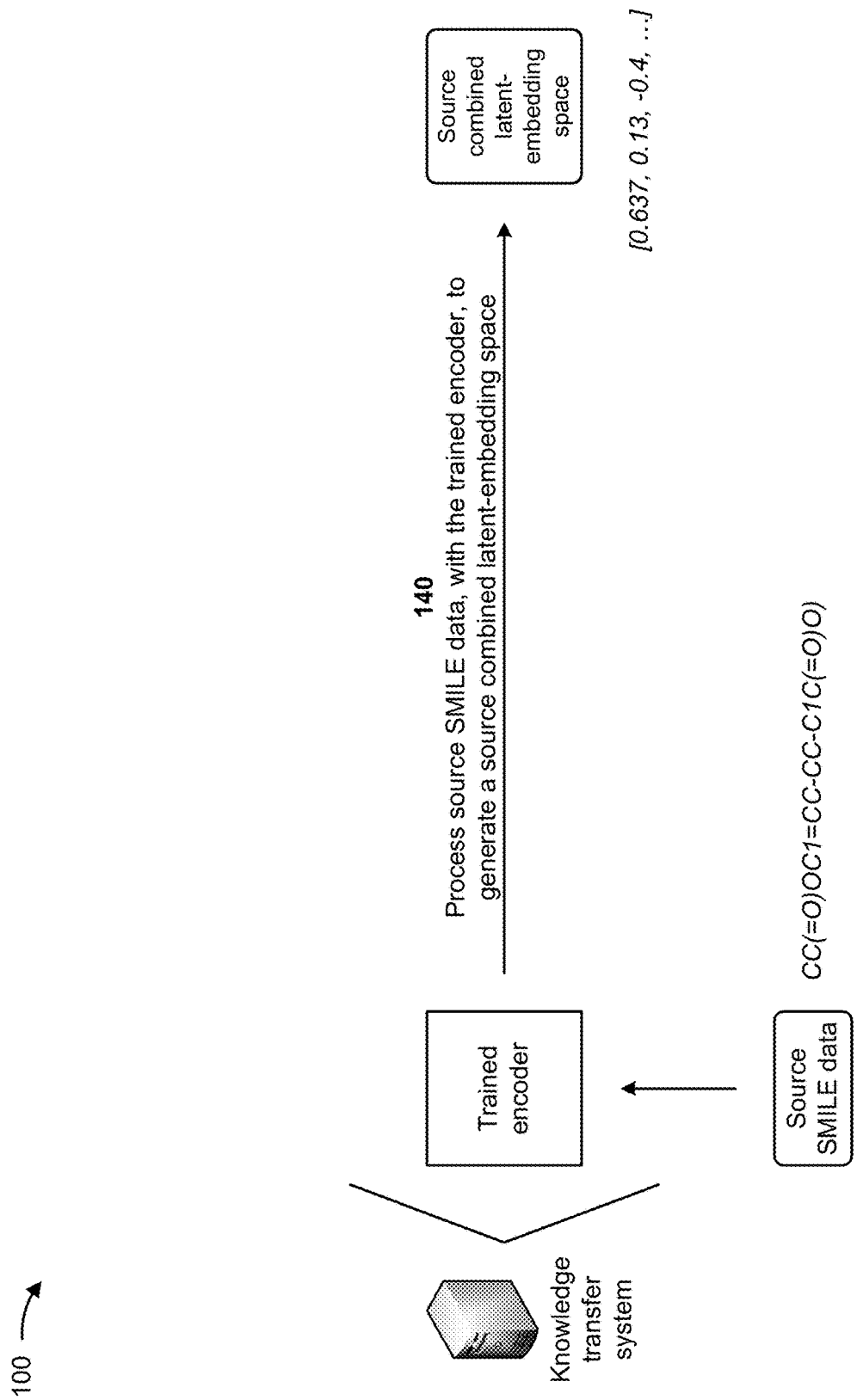

As shown in FIG. 1G, and by reference number 140, the knowledge transfer system may process source SMILE data, with the trained encoder, to generate a source combined latent-embedding space. For example, the source SMILE data may be associated with an existing compound that is known to combat a disease or an ailment. The knowledge transfer system may identify the source SMILE data, and may process the source SMILE data, with the trained encoder, to generate a source combined latent-embedding space. In some implementations, the trained encoder may generate source graph embeddings for the source SMILE data, and may combine the source graph embeddings and the latent space to generate the source combined latent-embedding space. This enables the source SMILE data to be represented as coordinates in the latent space that was trained using the graph embeddings, as described above. In some implementations, areas around the coordinates may include similar properties to the source SMILE data but may be associated with different compounds.

Figure 1H:
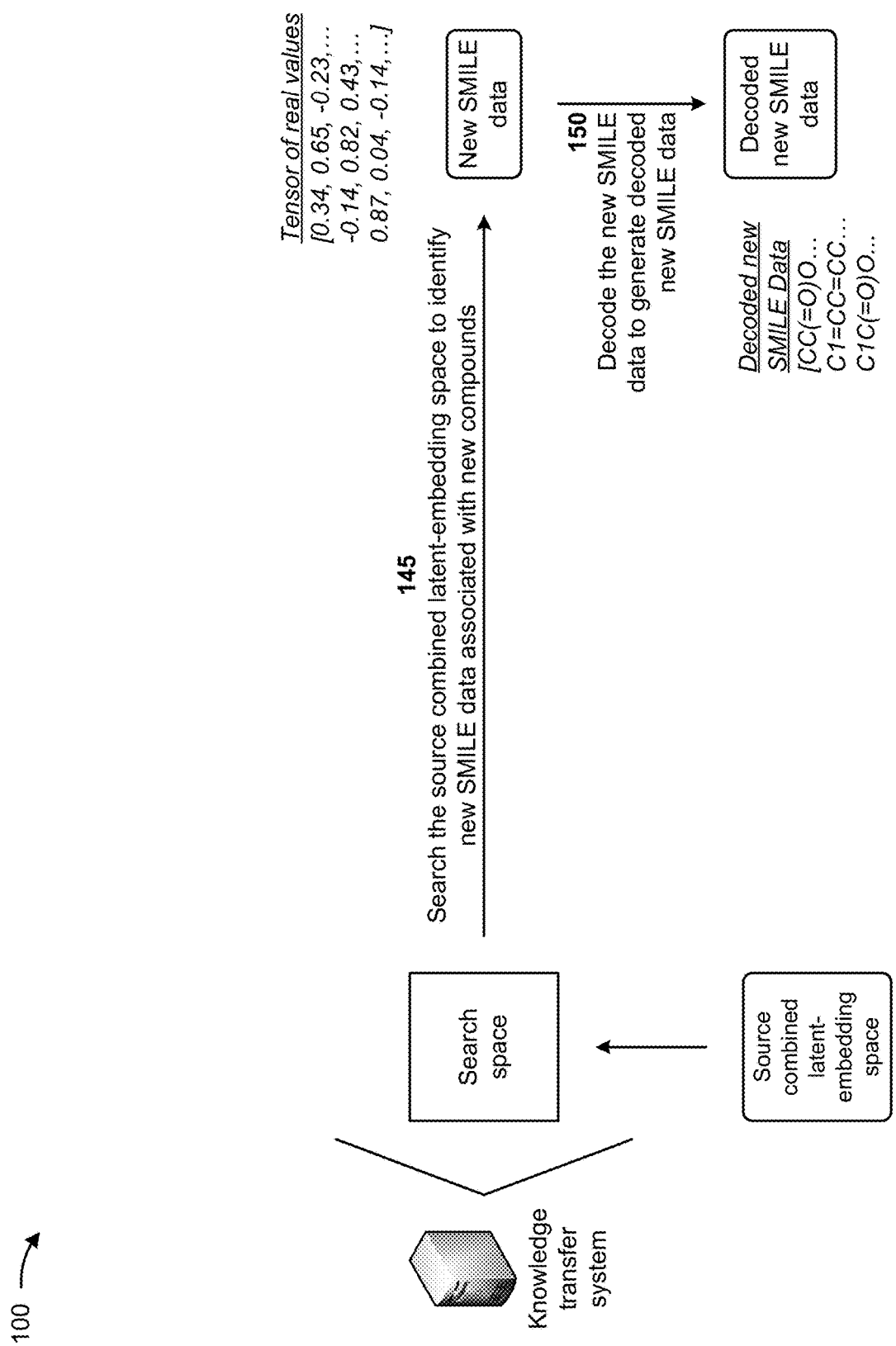

As shown in FIG. 1H, and by reference number 145, the knowledge transfer system may search the source combined latent-embedding space to identify new SMILE data associated with new compounds. For example, the knowledge transfer system may utilize interpolation to traverse between two known locations in the source combined latent-embedding space. The knowledge transfer system may utilize various search techniques to search the source combined latent-embedding space to identify the new SMILE data associated with the new compounds. Since the source combined latent-embedding space is created using graph embeddings, the knowledge transfer system may utilize a local search to identify the new SMILE data (e.g., with similar properties). In some implementations, when searching the source combined latent-embedding space to identify the new SMILE data associated with the new compounds, the knowledge transfer system may utilize linear interpolation to search the source combined latent-embedding space to identify the new SMILE data associated with the new compounds, may utilize spherical interpolation to search the source combined latent-embedding space to identify the new SMILE data associated with the new compounds, utilize random walk to search the source combined latent-embedding space to identify the new SMILE data associated with the new compounds, and/or the like.

As further shown in FIG. 1H, and by reference number 150, the knowledge transfer system may decode the new SMILE data to generate decoded new SMILE data. For example, the knowledge transfer system may train a decoder to convert the tensors provided in the source combined latent-embedding space back into compound specifications associated with the new compounds. The compound specifications may include the decoded new SMILE data of new compounds.

Figure 1I:
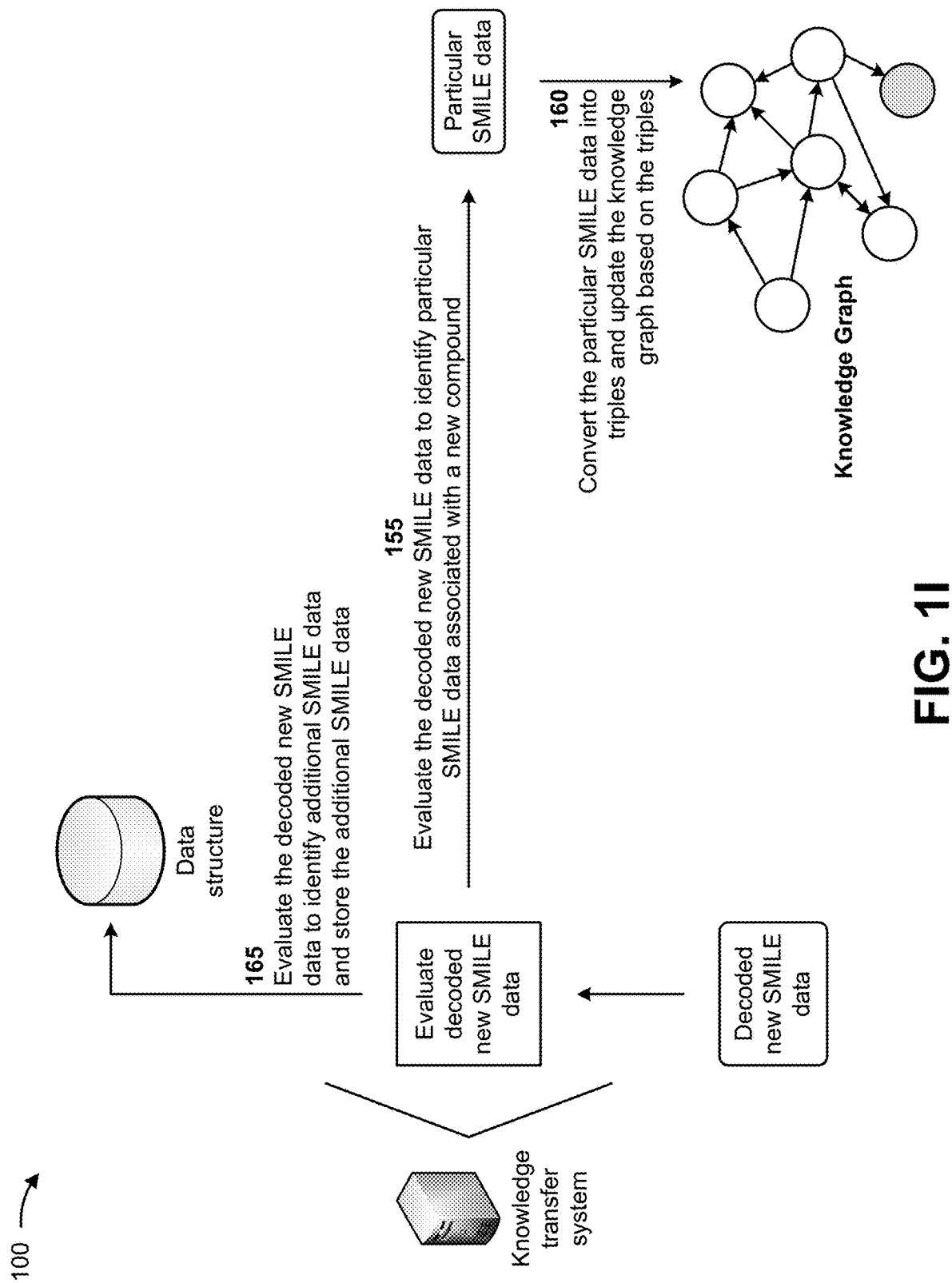

As shown in FIG. 1I, and by reference number 155, the knowledge transfer system may evaluate the decoded new SMILE data to identify particular SMILE data associated with a new compound. For example, the knowledge transfer system may evaluate the decoded new SMILE data with trained models that predict properties about SMILE data or by calculating heuristics using heuristic techniques. In some implementations, when evaluating the decoded new SMILE data to identify the particular SMILE data associated with the new compound, the knowledge transfer system may evaluate the decoded new SMILE data, with a trained machine learning model, to identify the particular SMILE data associated with the new compound, may evaluate the decoded new SMILE data, with a toolkit for chemical informatics, to identify the particular SMILE data associated with the new compound, may evaluate the decoded new SMILE data, with a toolkit for supra-molecular assembly, to identify the particular SMILE data associated with the new compound, and/or the like. In some implementations, experts may perform a manual inspection of the particular SMILE data.

As further shown in FIG. 1I, and by reference number 160, the knowledge transfer system may convert the particular SMILE data into triples and update the knowledge graph based on the triples. For example, if the evaluations of the models, the heuristics, and/or the experts satisfy a confidence threshold, the particular SMILE data may be added to the knowledge graph. The knowledge transfer system may convert the particular SMILE data into triples and may update the knowledge with the triples (e.g., may add the triples to the knowledge graph). In one example, the triples may include the following information:

| Subject | Predicate | Object |
| --- | --- | --- |
| Discovered drug 1 | has SMILE | CC(=O)OC1=CC=CC=C1C(=O)O |
| Discovered drug 1 | has drug likeness | 0.8 |
| Discovered drug 1 | has ease of synthesis | 0.9 |
| Discovered drug 1 | treats | fever |
| Discovered drug 1 | treats | arthritis |

As further shown in FIG. 1I, and by reference number 165, the knowledge transfer system may evaluate the decoded new SMILE data to identify additional SMILE data and may store the additional SMILE data. For example, if the evaluations of the models, the heuristics, and/or the experts fail to satisfy the confidence threshold, the knowledge transfer system may evaluate the decoded new SMILE data to identify the additional SMILE data and may store the additional SMILE data in the data structure for manual testing in a laboratory.

In this way, the knowledge transfer system transfers information through knowledge graph embeddings. The knowledge transfer system may represent all properties of SMILE data in a knowledge graph, and may reduce and represent all the properties in knowledge graph embeddings. Each of the knowledge graph embeddings may include the SMILE data in a vector of specified size. The knowledge transfer system may train a latent space to represent a structure of a property (e.g., a graph embedding) that includes all the properties of the SMILE data. The knowledge transfer system may generate the latent space based on all the properties of the SMILE data in a scalable and efficient manner. This, in turn, conserves computing resources, networking resources, and/or the like that would otherwise have been consumed in improperly training a machine learning model, failing to identify new drugs based on the improperly trained machine learning model, incorrectly identifying new drugs based on the improperly trained machine learning model, performing useless research and development on incorrectly identified new drugs, and/or the like.

As indicated above, FIGS. 1A-1I are provided as an example. Other examples may differ from what is described with regard to FIGS. 1A-1I. The number and arrangement of devices shown in FIGS. 1A-1I are provided as an example. In practice, there may be additional devices, fewer devices, different devices, or differently arranged devices than those shown in FIGS. 1A-1I. Furthermore, two or more devices shown in FIGS. 1A-1I may be implemented within a single device, or a single device shown in FIGS. 1A-1I may be implemented as multiple, distributed devices. Additionally, or alternatively, a set of devices (e.g., one or more devices) shown in FIGS. 1A-1I may perform one or more functions described as being performed by another set of devices shown in FIGS. 1A-1I.

FIG. 2 is a diagram of an example environment 200 in which systems and/or methods described herein may be implemented. As shown in FIG. 2, the environment 200 may include a knowledge transfer system 201, which may include one or more elements of and/or may execute within a cloud computing system 202. The cloud computing system 202 may include one or more elements 203-213, as described in more detail below. As further shown in FIG. 2, the environment 200 may include a network 220 and/or a data structure 230. Devices and/or elements of the environment 200 may interconnect via wired connections and/or wireless connections.

The cloud computing system 202 includes computing hardware 203, a resource management component 204, a host operating system (OS) 205, and/or one or more virtual computing systems 206. The resource management component 204 may perform virtualization (e.g., abstraction) of the computing hardware 203 to create the one or more virtual computing systems 206. Using virtualization, the resource management component 204 enables a single computing device (e.g., a computer, a server, and/or the like) to operate like multiple computing devices, such as by creating multiple isolated virtual computing systems 206 from the computing hardware 203 of the single computing device. In this way, the computing hardware 203 can operate more efficiently, with lower power consumption, higher reliability, higher availability, higher utilization, greater flexibility, and lower cost than using separate computing devices.

The computing hardware 203 includes hardware and corresponding resources from one or more computing devices. For example, the computing hardware 203 may include hardware from a single computing device (e.g., a single server) or from multiple computing devices (e.g., multiple servers), such as multiple computing devices in one or more data centers. As shown, the computing hardware 203 may include one or more processors 207, one or more memories 208, one or more storage components 209, and/or one or more networking components 210. Examples of a processor, a memory, a storage component, and a networking component (e.g., a communication component) are described elsewhere herein.

The resource management component 204 includes a virtualization application (e.g., executing on hardware, such as the computing hardware 203) capable of virtualizing the computing hardware 203 to start, stop, and/or manage the one or more virtual computing systems 206. For example, the resource management component 204 may include a hypervisor (e.g., a bare-metal or Type 1 hypervisor, a hosted or Type 2 hypervisor, and/or the like) or a virtual machine monitor, such as when the virtual computing systems 206 are virtual machines 211. Additionally, or alternatively, the resource management component 204 may include a container manager, such as when the virtual computing systems 206 are containers 212. In some implementations, the resource management component 204 executes within and/or in coordination with a host operating system 205.

A virtual computing system 206 includes a virtual environment that enables cloud-based execution of operations and/or processes described herein using computing hardware 203. As shown, a virtual computing system 206 may include a virtual machine 211, a container 212, a hybrid environment 213 that includes a virtual machine and a container, and/or the like. A virtual computing system 206 may execute one or more applications using a file system that includes binary files, software libraries, and/or other resources required to execute applications on a guest operating system (e.g., within the virtual computing system 206) or the host operating system 205.

Although the knowledge transfer system 201 may include one or more elements 203-213 of the cloud computing system 202, may execute within the cloud computing system 202, and/or may be hosted within the cloud computing system 202, in some implementations, the knowledge transfer system 201 may not be cloud-based (e.g., may be implemented outside of a cloud computing system) or may be partially cloud-based. For example, the knowledge transfer system 201 may include one or more devices that are not part of the cloud computing system 202, such as device 300 of FIG. 3, which may include a standalone server or another type of computing device. The knowledge transfer system 201 may perform one or more operations and/or processes described in more detail elsewhere herein.

The network 220 includes one or more wired and/or wireless networks. For example, the network 220 may include a cellular network, a public land mobile network (PLMN), a local area network (LAN), a wide area network (WAN), a private network, the Internet, and/or the like, and/or a combination of these or other types of networks. The network 220 enables communication among the devices of the environment 200.

The data structure 230 may include one or more devices capable of receiving, generating, storing, processing, and/or providing information, as described elsewhere herein. The data structure 230 may include a communication device and/or a computing device. For example, the data structure 230 may include a database, a server, a database server, an application server, a client server, a web server, a host server, a proxy server, a virtual server (e.g., executing on computing hardware), a server in a cloud computing system, a device that includes computing hardware used in a cloud computing environment, or a similar type of device. The data structure 230 may communicate with one or more other devices of the environment 200, as described elsewhere herein.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of the environment 200 may perform one or more functions described as being performed by another set of devices of the environment 200.

FIG. 3 is a diagram of example components of a device 300, which may correspond to the knowledge transfer system 201 and/or the data structure 230. In some implementations, the knowledge transfer system 201 and/or the data structure 230 may include one or more devices 300 and/or one or more components of the device 300. As shown in FIG. 3, the device 300 may include a bus 310, a processor 320, a memory 330, an input component 340, an output component 350, and a communication component 360.

The bus 310 includes a component that enables wired and/or wireless communication among the components of device 300. The processor 320 includes a central processing unit, a graphics processing unit, a microprocessor, a controller, a microcontroller, a digital signal processor, a field-programmable gate array, an application-specific integrated circuit, and/or another type of processing component. The processor 320 is implemented in hardware, firmware, or a combination of hardware and software. In some implementations, the processor 320 includes one or more processors capable of being programmed to perform a function. The memory 330 includes a random-access memory, a read only memory, and/or another type of memory (e.g., a flash memory, a magnetic memory, and/or an optical memory).

The input component 340 enables the device 300 to receive input, such as user input and/or sensed inputs. For example, the input component 340 may include a touch screen, a keyboard, a keypad, a mouse, a button, a microphone, a switch, a sensor, a global positioning system component, an accelerometer, a gyroscope, an actuator, and/or the like. The output component 350 enables the device 300 to provide output, such as via a display, a speaker, and/or one or more light-emitting diodes. The communication component 360 enables the device 300 to communicate with other devices, such as via a wired connection and/or a wireless connection. For example, the communication component 360 may include a receiver, a transmitter, a transceiver, a modem, a network interface card, an antenna, and/or the like.

The device 300 may perform one or more processes described herein. For example, a non-transitory computer-readable medium (e.g., the memory 330) may store a set of instructions (e.g., one or more instructions, code, software code, program code, and/or the like) for execution by the processor 320. The processor 320 may execute the set of instructions to perform one or more processes described herein. In some implementations, execution of the set of instructions, by one or more processors 320, causes the one or more processors 320 and/or the device 300 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 3 are provided as an example. The device 300 may include additional components, fewer components, different components, or differently arranged components than those shown in FIG. 3. Additionally, or alternatively, a set of components (e.g., one or more components) of the device 300 may perform one or more functions described as being performed by another set of components of the device 300.

Figure 4:
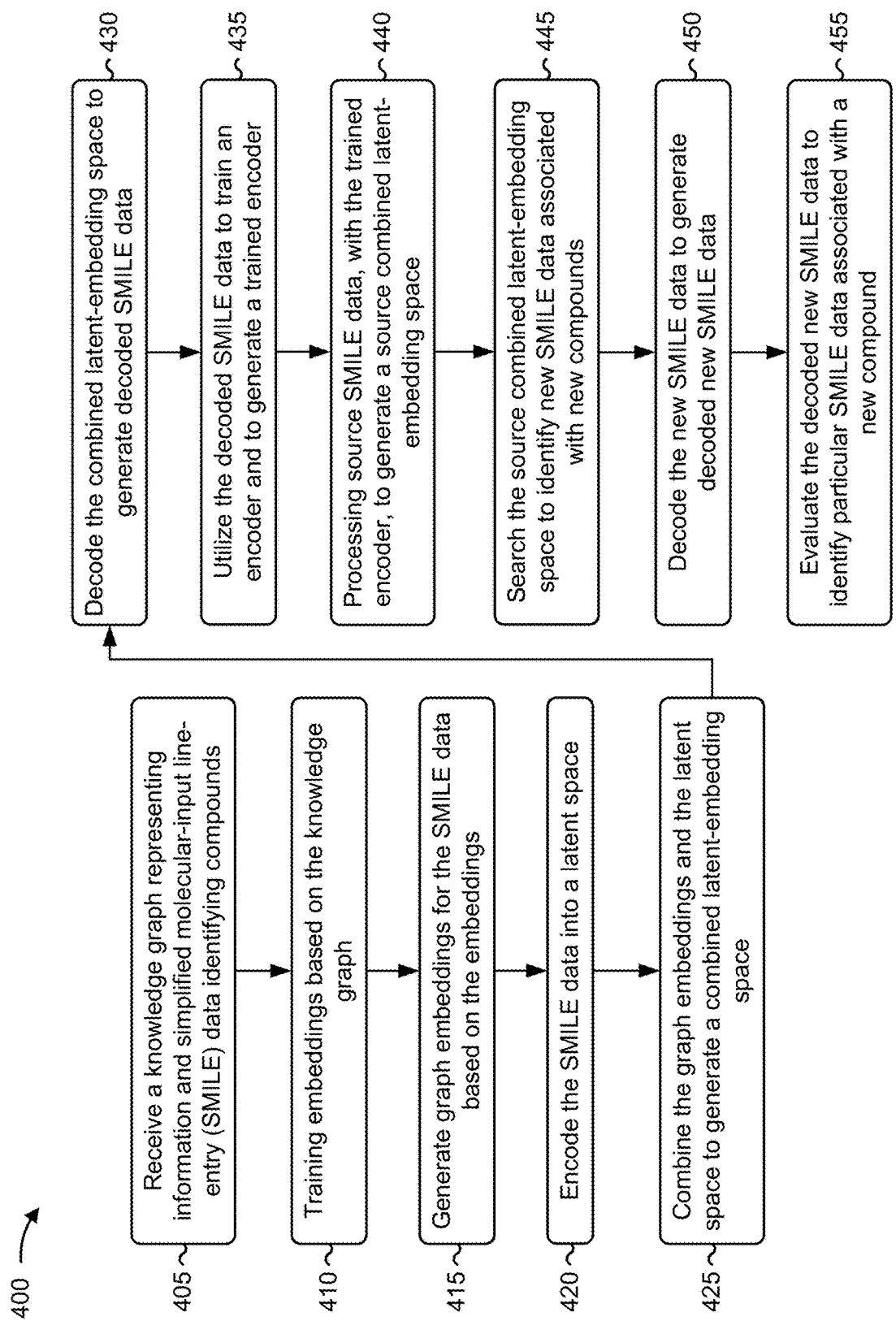
FIG. 4 is a flowchart of an example process for transferring information through knowledge graph embeddings.

FIG. 4 is a flowchart of an example process 400 for transferring information through knowledge graph embeddings. In some implementations, one or more process blocks of FIG. 4 may be performed by a device (e.g., the knowledge transfer system 201). In some implementations, one or more process blocks of FIG. 4 may be performed by another device or a group of devices separate from or including the device. Additionally, or alternatively, one or more process blocks of FIG. 4 may be performed by one or more components of the device 300, such as the processor 320, the memory 330, the input component 340, the output component 350, and/or the communication component 360.

As shown in FIG. 4, process 400 may include receiving a knowledge graph representing information and SMILE data identifying compounds (block 405). For example, the device may receive a knowledge graph representing information and SMILE data identifying compounds, as described above. In some implementations, the knowledge graph includes representations of compounds, and data identifying diseases treated by the compounds or biological pathways of the compounds.

As further shown in FIG. 4, process 400 may include training, by the device, embeddings based on the knowledge graph (block 410). For example, the device may training, by the device, embeddings based on the knowledge graph, as described above. In some implementations, training the embeddings based on the knowledge graph includes training the embeddings with a neural tensor network with a diagonal matrix operator, training the embeddings with a holographic embeddings technique, training the embeddings with a convolutional two-dimensional knowledge graph embeddings technique, or training the embeddings with a complex embeddings technique.

As further shown in FIG. 4, process 400 may include generating graph embeddings for the SMILE data based on the embeddings (block 415). For example, the device may generate graph embeddings for the SMILE data based on the embeddings, as described above. In some implementations, the graph embeddings cluster similar compounds together in the latent space based on properties of the similar compounds in the knowledge graph. In some implementations, dimensions of the graph embeddings are equivalent to dimensions of the latent space.

As further shown in FIG. 4, process 400 may include encoding the SMILE data into a latent space (block 420). For example, the device may encode the SMILE data into a latent space, as described above. In some implementations, encoding the SMILE data into the latent space includes encoding the SMILE data into the latent space via a variational autoencoder, encoding the SMILE data into the latent space via an adversarial autoencoder, or encoding the SMILE data into the latent space via a generative adversarial network. In some implementations, the latent space clusters similar compounds together based on the SMILE data.

As further shown in FIG. 4, process 400 may include combining the graph embeddings and the latent space to generate a combined latent-embedding space (block 425). For example, the device may combine the graph embeddings and the latent space to generate a combined latent-embedding space, as described above. In some implementations, combining the graph embeddings and the latent space to generate the combined latent-embedding space includes processing the graph embeddings and the latent space, with a deep learning model, to generate the combined latent-embedding space.

As further shown in FIG. 4, process 400 may include decoding the combined latent-embedding space to generate decoded SMILE data (block 430). For example, the device may decode the combined latent-embedding space to generate decoded SMILE data, as described above.

As further shown in FIG. 4, process 400 may include utilizing the decoded SMILE data to train an encoder and to generate a trained encoder (block 435). For example, the device may utilize the decoded SMILE data to train an encoder and to generate a trained encoder, as described above.

As further shown in FIG. 4, process 400 may include processing, by the device, source SMILE data, with the trained encoder, to generate a source combined latent-embedding space (block 440). For example, the device may process source SMILE data, with the trained encoder, to generate a source combined latent-embedding space, as described above.

As further shown in FIG. 4, process 400 may include searching the source combined latent-embedding space to identify new SMILE data associated with new compounds (block 445). For example, the device may search the source combined latent-embedding space to identify new SMILE data associated with new compounds, as described above. In some implementations, searching the source combined latent-embedding space to identify the new SMILE data associated with the new compounds includes utilizing linear interpolation to search the source combined latent-embedding space to identify the new SMILE data associated with the new compounds, utilizing spherical interpolation to search the source combined latent-embedding space to identify the new SMILE data associated with the new compounds, or utilizing random walk to search the source combined latent-embedding space to identify the new SMILE data associated with the new compounds.

As further shown in FIG. 4, process 400 may include decoding the new SMILE data to generate decoded new SMILE data (block 450). For example, the device may decode the new SMILE data to generate decoded new SMILE data, as described above.

As further shown in FIG. 4, process 400 may include evaluating the decoded new SMILE data to identify particular SMILE data associated with a new compound (block 455). For example, the device may evaluate the decoded new SMILE data to identify particular SMILE data associated with a new compound, as described above. In some implementations, evaluating the decoded new SMILE data to identify the particular SMILE data associated with the new compound includes evaluating the decoded new SMILE data, with a trained machine learning model, to identify the particular SMILE data associated with the new compound, evaluating the decoded new SMILE data, with a toolkit for chemical informatics, to identify the particular SMILE data associated with the new compound, or evaluating the decoded new SMILE data, with a toolkit for supra-molecular assembly, to identify the particular SMILE data associated with the new compound.

In some implementations, process 400 includes converting the particular SMILE data into triples, and updating the knowledge graph based on the triples. In some implementations, each of the triples includes data identifying a subject, a predicate, and an object. In some implementations, process 400 includes evaluating the decoded new SMILE data to identify additional SMILE data, and storing the additional SMILE data.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, and/or the like, depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising:
   receiving, by a device, a knowledge graph representing information and simplified molecular-input line-entry (SMILE) data identifying compounds;
   training, by the device, embeddings based on the knowledge graph;
   generating, by the device, graph embeddings for the SMILE data based on the embeddings;
   encoding, by the device, the SMILE data into a latent space;
   combining, by the device, the graph embeddings and the latent space to generate a combined latent-embedding space;

decoding, by the device, the combined latent-embedding
space to generate decoded SMILE data;
utilizing, by the device, the decoded SMILE data to train
an encoder and to generate a trained encoder;
processing, by the device, source SMILE data, with the
trained encoder, to generate a source combined latent-
embedding space;
searching, by the device, the source combined latent-
embedding space to identify new SMILE data associ-
ated with new compounds;
decoding, by the device, the new SMILE data to generate
decoded new SMILE data; and
evaluating, by the device, the decoded new SMILE data
to identify particular SMILE data associated with a new
compound.

2. The method of claim 1, further comprising:
converting the particular SMILE data into triples; and
updating the knowledge graph based on the triples.

3. The method of claim 2, wherein each of the triples includes data identifying a subject, a predicate, and an object.

4. The method of claim 1, further comprising:
evaluating the decoded new SMILE data to identify additional SMILE data; and
storing the additional SMILE data.

5. The method of claim 1, wherein training the embeddings based on the knowledge graph comprises one or more of:
training the embeddings with a neural tensor network with a diagonal matrix operator;
training the embeddings with a holographic embeddings technique;
training the embeddings with a convolutional two-dimensional knowledge graph embeddings technique; or
training the embeddings with a complex embeddings technique.

6. The method of claim 1, wherein the graph embeddings cluster similar compounds together in the latent space based on properties of the similar compounds in the knowledge graph.

7. The method of claim 1, wherein encoding the SMILE data into the latent space comprises one or more of:
encoding the SMILE data into the latent space via a variational autoencoder;
encoding the SMILE data into the latent space via an adversarial autoencoder; or
encoding the SMILE data into the latent space via a generative adversarial network.

8. A device, comprising:
one or more memories; and
one or more processors, coupled to the one or more memories, configured to:
receive a knowledge graph representing information and simplified molecular-input line-entry (SMILE) data identifying compounds;
train embeddings based on the knowledge graph;
generate graph embeddings for the SMILE data based on the embeddings;
encode the SMILE data into a latent space;
combine the graph embeddings and the latent space to generate a combined latent-embedding space;
decode the combined latent-embedding space to generate decoded SMILE data;
utilize the decoded SMILE data to train an encoder and to generate a trained encoder;
process source SMILE data, with the trained encoder, to generate a source combined latent-embedding space;
search the source combined latent-embedding space to identify new SMILE data associated with new compounds;
decode the new SMILE data to generate decoded new SMILE data;
evaluate the decoded new SMILE data to identify particular SMILE data associated with a new compound;
convert the particular SMILE data into triples; and
update the knowledge graph based on the triples.

9. The device of claim 8, wherein the latent space clusters similar compounds together based on the SMILE data.

10. The device of claim 8, wherein the one or more processors, to combine the graph embeddings and the latent space to generate the combined latent-embedding space, are configured to:
process the graph embeddings and the latent space, with a deep learning model, to generate the combined latent-embedding space.

11. The device of claim 8, wherein the one or more processors, to search the source combined latent-embedding space to identify the new SMILE data associated with the new compounds, are configured to one or more of:
utilize linear interpolation to search the source combined latent-embedding space to identify the new SMILE data associated with the new compounds;
utilize spherical interpolation to search the source combined latent-embedding space to identify the new SMILE data associated with the new compounds; or
utilize random walk to search the source combined latent-embedding space to identify the new SMILE data associated with the new compounds.

12. The device of claim 8, wherein the one or more processors, to evaluate the decoded new SMILE data to identify the particular SMILE data associated with the new compound, are configured to one or more of:
evaluate the decoded new SMILE data, with a trained machine learning model, to identify the particular SMILE data associated with the new compound;
evaluate the decoded new SMILE data, with a toolkit for chemical informatics, to identify the particular SMILE data associated with the new compound; or
evaluate the decoded new SMILE data, with a toolkit for supra-molecular assembly, to identify the particular SMILE data associated with the new compound.

13. The device of claim 8, wherein the knowledge graph includes:
representations of compounds, and
data identifying diseases treated by the compounds or biological pathways of the compounds.

14. The device of claim 8, wherein dimensions of the graph embeddings are equivalent to dimensions of the latent space.

15. A non-transitory computer-readable medium storing a set of instructions, the set of instructions comprising:
one or more instructions that, when executed by one or more processors of a device, cause the device to:
receive a knowledge graph representing information and simplified molecular-input line-entry (SMILE) data identifying compounds;
train embeddings based on the knowledge graph;
generate graph embeddings for the SMILE data based on the embeddings;
encode the SMILE data into a latent space;

combine the graph embeddings and the latent space to generate a combined latent-embedding space;

decode the combined latent-embedding space to generate decoded SMILE data;

utilize the decoded SMILE data to train an encoder and to generate a trained encoder;

process source SMILE data, with the trained encoder, to generate a source combined latent-embedding space;

search the source combined latent-embedding space to identify new SMILE data associated with new compounds;

decode the new SMILE data to generate decoded new SMILE data;

evaluate the decoded new SMILE data to identify particular SMILE data associated with a new compound;

convert the particular SMILE data into triples;

update the knowledge graph based on the triples;

evaluate the decoded new SMILE data to identify additional SMILE data; and store the additional SMILE data.

16. The non-transitory computer-readable medium of claim 15, wherein the one or more instructions, that cause the device to train the embeddings based on the knowledge graph, cause the device to one or more of:

train the embeddings with a neural tensor network with a diagonal matrix operator;

train the embeddings with a holographic embeddings technique;

train the embeddings with a convolutional two-dimensional knowledge graph embeddings technique; or train the embeddings with a complex embeddings technique.

17. The non-transitory computer-readable medium of claim 15, wherein the one or more instructions, that cause the device to encode the SMILE data into the latent space, cause the device to one or more of:

encode the SMILE data into the latent space via a variational autoencoder;

encode the SMILE data into the latent space via an adversarial autoencoder; or encode the SMILE data into the latent space via a generative adversarial network.

18. The non-transitory computer-readable medium of claim 15, wherein the one or more instructions, that cause the device to combine the graph embeddings and the latent space to generate the combined latent-embedding space, cause the device to:

process the graph embeddings and the latent space, with a deep learning model, to generate the combined latent-embedding space.

19. The non-transitory computer-readable medium of claim 15, wherein the one or more instructions, that cause the device to search the source combined latent-embedding space to identify the new SMILE data associated with the new compounds, cause the device to one or more of:

utilize linear interpolation to search the source combined latent-embedding space to identify the new SMILE data associated with the new compounds;

utilize spherical interpolation to search the source combined latent-embedding space to identify the new SMILE data associated with the new compounds; or utilize random walk to search the source combined latent-embedding space to identify the new SMILE data associated with the new compounds.

20. The non-transitory computer-readable medium of claim 15, wherein the one or more instructions, that cause the device to evaluate the decoded new SMILE data to identify the particular SMILE data associated with the new compound, cause the device to one or more of:

evaluate the decoded new SMILE data, with a trained machine learning model, to identify the particular SMILE data associated with the new compound;

evaluate the decoded new SMILE data, with a toolkit for chemical informatics, to identify the particular SMILE data associated with the new compound; or evaluate the decoded new SMILE data, with a toolkit for supra-molecular assembly, to identify the particular SMILE data associated with the new compound.

* * * * *